US000001541H

United States Statutory Invention Registration [19]

[11] Reg. Number: H1541

Holla

[45] Published: Jun. 4, 1996

[54] METHOD FOR PRODUCING AZADIRACHTIN CONCENTRATES FROM NEEM SEED MATERIALS

[76] Inventor: Kadambar S. Holla, Tata Oil Mills Co., Ltd, Hay Bunder Road, Sewri Bombay 400033, India

[21] Appl. No.: 94,779

[22] Filed: Jul. 21, 1993

[51] Int. Cl.[6] ..... A01N 65/00; A01N 43/16; A61K 35/78; A61K 31/35

[52] U.S. Cl. ..... 424/195.1; 514/453

[58] Field of Search ..... 424/195.1; 514/453

[56] References Cited

U.S. PATENT DOCUMENTS

| | | | |
|---|---|---|---|
| 4,556,562 | 12/1985 | Larson | 424/195.1 |
| 4,946,681 | 8/1990 | Walter | 424/195.1 |
| 5,001,146 | 3/1991 | Carter et al. | 514/453 |
| 5,124,349 | 6/1992 | Carter et al. | 514/453 |

FOREIGN PATENT DOCUMENTS

WO92/16109 10/1992 WIPO .

OTHER PUBLICATIONS

Schroeder et al; J. Nat. Prod. 50(2):241–244 (1987).

J. H. Butterworth and E. D. Morgan, "Investigation of the Locust Feeding Inhibition of the Seeds of the Neem Tree, *Azadirachta Indica*", J. Insect Physiol., 1971, vol. 17, pp. 969–977.

*Primary Examiner*—Charles T. Jordan
*Assistant Examiner*—John R. Hardee

[57] ABSTRACT

The present invention provides a method for producing an azadirachtin concentrate by extracting azadirachtin-containing oils from plant materials, and precipitating the azadirachtin from the oils using a non-polar solvent in which azadirachtin has low solubility.

34 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD FOR PRODUCING AZADIRACHTIN CONCENTRATES FROM NEEM SEED MATERIALS

FIELD OF THE INVENTION

This invention relates to a method for obtaining azadirachtin concentrates from azadirachtin-containing materials. More particularly, this invention relates to a method for producing an azadirachtin concentrate by extracting azadirachtin-containing oils from plant materials and precipitating the azadirachtin from the oils using a non-polar solvent.

BACKGROUND OF THE INVENTION

Extracts of the neem tree (*Azadirachta indica*), the chinaberry tree (*Melia azedarach*), and other plants in the family Meliaceae (e.g. *Azadirachta excelsa*) have long been known to have insecticidal activity (Natural Pesticides from the Neem Tree, Proc. 1st Int'l Neem Conf. 1980 [H. Schmutterer et al. eds. 1982]; Natural Pesticides from the Neem Tree and Other Tropical Plants, Proc. 2nd Int'l Neem Conf. 1983 [H. Schmutterer and K. R. S. Asher eds. 1984]; Natural Pesticides from the Neem Tree and Other Tropical Plants, Proc. 3rd Int'l Neem Conf. 1986 [H. Schmutterer and K. R. S. Asher eds. 1987]). Azadirachtin, a major active ingredient in many of these extracts, is a limonoid of the tetranortriterpenoid type. Azadirachtin has been shown to be a potent insect growth regulator and feeding deterrent with value as an active ingredient in commercial insecticides (R. B. Yamasaki et al. (1987) J. Agric. Food Chem. 35:467–471).

The use of azadirachtin in commercial insecticides requires that the compound be extracted from the plant material and concentrated in a convenient form. Suitable azadirachtin concentrates are solid in form, have high levels of azadirachtin (typically greater than 1–3% by weight), and contain little or no plant oils and water. These characteristics facilitate handling, storage, distribution, and formulation.

Various methods of extracting azadirachtin from neem seeds are known in the art. J. H. Butterworth and E. D. Morgan, (1971) J. Insect. Physiol. 17:969–977, describe the extraction of azadirachtin and neem oil from neem seeds using ethanol, a common solvent for azadirachtin isolation. Further separation steps (including filtration, partition of the soluble portion between light petroleum and methanol, and chromatography of the methanol extract on Floridin earth) are used to concentrate the azadirachtin to obtain a solid. Larson (U.S. Pat. No. 4,556,562) discloses a similar method whereby neem seeds are first reduced in size to that of a regular grind of coffee. Azadirachtin is then extracted at elevated temperatures, again using ethanol. No further concentration steps are used, however, and the final extract is a liquid containing only 0.5–1% azadirachtin. Walter (U.S. Pat. No. 4,946,681) describes a related process for extracting azadirachtin from ground de-oiled neem seeds with aprotic solvents or alcohols. The liquid extract is further treated with molecular sieves to remove water. Carter et al. (U.S. Pat. No. 5,001,146) describes a two-step extraction process comprising a "cleanup" extraction with a non-polar aprotic solvent to remove the neem oil from the seeds, followed by a second extraction of the defatted neem seeds using a more polar, azadirachtin-soluble solvent. The final extract from this process is a solution containing about 4.5 g/l azadirachtin. Kleeberg (WO 92/16109) also describes a multi-step procedure whereby the azadirachtin is first extracted from neem oil and plant material using water. The aqueous fraction is then extracted with an organic solvent to remove the azadirachtin from the water. A solid azadirachtin concentrate is ultimately obtained using a slow and inefficient phase separation followed by concentration of the organic phase and crystallization.

Inefficiencies and limitations associated with the processes described above illustrate the need for more practical and versatile methods for obtaining azadirachtin concentrates. Specifically, current methods that produce extracts containing suitably high azadirachtin content (>1–3% by weight) all involve expensive steps to remove neem oil, water, and other impurities. Such steps include decantation, phase separation, chromatography, crystallization, treatment with molecular sieves, and other purification steps. None of the known methods provides a suitably efficient, economical, or practical means for recovering azadirachtin in a concentrated solid form that contains little or no neem oil or water.

The present invention solves these problems by employing a simple and efficient precipitation step that produces an azadirachtin concentrate which is easily and efficiently separated from plant oils and other non-polar plant components. The present invention thus represents a significant improvement over the prior art methods.

SUMMARY OF THE INVENTION

The present invention provides a practical and efficient process for producing an azadirachtin concentrate from azadirachtin-containing materials. The process, in accordance with the invention, is carried out by preparing an azadirachtin-containing plant oil and/or plant extract, then precipitating the azadirachtin and other polar compounds from the oil and/or extract with a non-polar solvent in which azadirachtin has low solubility.

Another principal object of the invention is to provide a method for recovering azadirachtin in a concentrated solid form rather than in a dilute solution. The azadirachtin concentrate produced according to the instant method can be readily collected and separated from the liquid fractions of the plant oil or extract.

Yet another object of the invention is its effectiveness in producing an azadirachtin-containing precipitate which can be readily separated from plant oils and other non-polar components of crude plant extracts.

Azadirachtin concentrates produced in accordance with the invention can be readily collected, dried and further processed. These concentrates have high levels of azadirachtin relative to the initial seed content. Such concentrates are convenient for storage and distribution purposes and are particularly suitable starting materials for azadirachtin-based products.

Other objects, features, and advantages of the present invention will become apparent from the following detailed description. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

The invention relates to a method for extracting azadirachtin from azadirachtin-containing plant materials. The invention is characterized by first obtaining azadirachtin-containing oils from said plant materials, preferably neem or chinaberry tree seeds, then precipitating the azadirachtin from the oils. The oil-producing step can be accomplished by mechanical and/or chemical means, i.e., using oil expelling equipment and/or solvent extraction, respectively. The azadirachtin is then precipitated from the expelled or extracted oil using a non-polar solvent in which azadirachtin has low solubility. As used herein, "non-polar solvents in which azadirachtin has low solubility" generally refers to non-polar solvents in which azadirachtin is less soluble than in mechanically expelled or chemically extracted neem oil.

As used herein, "expelled oil" and "mechanically expelled oil" refer to oils that are removed from plant material using mechanical expelling techniques. Mechanical expelling in accordance with the present invention produces "expelled oil" and "expeller cake".

Also as used herein, "extracted oil," "chemically extracted oil," "solvent extracted oil," and "plant extract" refer to oil-bearing extracts that are removed from plant materials using solvent extraction techniques.

"Plant oil" and "neem oil" generally refer to oils that are removed from plant materials and neem materials, respectively, using mechanical and/or solvent extraction techniques.

As used herein, "azadirachtin-containing precipitate," "azadirachtin-containing concentrate," and "azadirachtin concentrate" refer to azadirachtin extracts comprising at least a ten-fold increase in percentage by weight of azadirachtin relative to the percentage by weight of azadirachtin in the plant material from which it is derived. Azadirachtin concentrates derived from neem seed kernel typically contain greater than 1–3% azadirachtin.

As briefly noted above, the azadirachtin concentrate produced by the present invention is obtained by extracting azadirachtin-containing oil from plant material by mechanical and/or chemical means, then precipitating the azadirachtin from the oil(s). In general, the process comprises the following steps:

(a) removing oil from seeds, kernel, or expeller cake by mechanical and/or chemical means;

(b) admixing the oil with a sufficient amount of a non-polar solvent in which azadirachtin has low solubility, preferably a hydrocarbon, to precipitate the azadirachtin and other polar components from the oil/solvent solution;

(c) isolating the azadirachtin-containing precipitate by vacuum filtration or centrifugation or other common separation methods; and optionally (d) drying the precipitate to remove residual solvent.

Specifically, at the outset of the process, the neem seeds are preferably dried and separated from unwanted debris, typically using vibrating screen shakers. The seed kernels are then released from the cleaned seeds, for example using a "roller cracker" or "knife blade" sheller, and separated from hull materials, again using vibrating screen shakers or similar devices. Cleaned neem seed kernels typically contain approximately 30–40% neem oil and 0.1–0.3% azadirachtin.

The step of producing oil from seed and/or kernel can be accomplished by either of two general procedures (mechanical or chemical), or a combination thereof.

A first embodiment of this invention is to extract azadirachtin-containing plant oil from plant materials, such as the neem seed kernel exemplified herein, using mechanical expelling techniques. The neem seed kernel fraction, prepared as described above, may be steamed or boiled to facilitate oil expelling. Mechanical expelling techniques are well known in the art. They include, but are not limited to, grinding, flaking or pressing. The equipment used in the expelling step is not critical, and most traditional oil expelling machinery that grinds, flakes and/or presses the seeds or kernels to provide an acceptable yield of oil is suitable.

The expelling step generates liquid plant oil and solid expeller cake. The oil carries a portion of the azadirachtin in solution. The expelled oil is preferably filtered to remove particulate matter using, for example, a plate and frame filter, centrifuge, or the like. If desired, the filtered particulate matter and/or the expeller cake can be passed through the expeller again to optimize yield. To further increase the yield of azadirachtin, the expeller cake and/or the filtered particulate matter can also be chemically processed, as described below.

A second embodiment of this invention is to chemically extract azadirachtin and plant oil together from the plant material by mixing said plant material with a polar solvent. The seed or kernel material is prepared as previously described. Preferably, it is also fractured or comminuted prior to extraction to improve extraction efficiency. Alternatively, the expeller cake produced during the mechanical expelling step can be further treated with a polar solvent to remove residual oil and azadirachtin.

As with mechanical expelling, the method of chemical extraction is not critical. Solvent extraction may be carried out as a batch process by admixing seed kernel or expeller cake with a suitable polar solvent until an acceptable amount of azadirachtin and oil is removed. As in the first embodiment, the polar solvent extraction can be repeated to optimize extraction efficiency. Solvent extraction can also be carried out as a continuous process, preferably in a fluid bed solvent extractor, again using a polar solvent. As will be apparent to those of ordinary skill in the art, efficiency of extraction can be enhanced by manipulating the extraction conditions, particularly the operating temperature and extraction time.

Solvent extraction is preferably carried out using ethylene dichloride or dichloromethane, which extract both azadirachtin and oil from plant material or expeller cake. A wide variety of other solvents may also be used with good results. Any solvent or combination of solvents which solubilizes or suspends azadirachtin and plant oil without causing the decomposition of azadirachtin is suitable. Suitable solvents for use in this invention include, but are not limited to, ketones, alcohols, esters, ethers, nitriles, amides, sulfoxides, substituted aliphatic hydrocarbons, aromatic hydrocarbons and substituted aromatic hydrocarbons, and mixtures thereof. Specific examples include acetone, benzene, dichloromethane, ethanol, ethyl acetate, ethylene dichloride, methanol, methyl acetate, methyl t-butyl ether, methyl formate, 2-propanol, toluene and xylene, and mixtures thereof. These solvents are relatively inexpensive and readily available.

Various techniques are available to reduce the concentration of polar solvent in the extracted oil mixture to acceptable levels prior to the final processing steps. Techniques include, but are not limited to, passage through solvent strippers. The low solvent level is generally accomplished by adjusting the number of stripper columns and/or the operating temperature and pressure (vacuum) of the columns.

The oil produced by mechanical expelling and/or solvent extraction techniques as described in the above embodiments is subsequently treated with a sufficient amount of a non-polar solvent to precipitate an azadirachtin concentrate.

The precipitation is generally accomplished by combining the expelled oil and/or extracted oils with a non-polar solvent and agitating the mixture in a vessel. The oil and other non-polar components remain in solution, while the more polar components, including azadirachtin, precipitate in solid form.

Azadirachtin precipitation is carried out using a non-polar solvent in which azadirachtin has low solubility. Any non-polar solvent or combination of solvents which precipitates azadirachtin is suitable. Preferred solvents are straight-chained, branched or cyclic derivatives of pentanes, hexanes, heptanes, octanes, nonanes and decanes, and mixtures thereof. Paraffin oils and aromatic hydrocarbons, including mixtures thereof, are also preferred. Most preferably, the solvents are hexanes, heptanes, and/or petroleum ethers. These solvents are relatively inexpensive and readily available.

Comparative studies were performed to test the effects of experimental conditions on azadirachtin yield. Although good results were obtained under a broad range of conditions, the examples show that various process parameters can be adjusted, if desired, to optimize precipitation efficiency. Specifically, the ratio of oil to solvent, the operating temperature and the addition rate of the reactants can be adjusted to maximize the yield of azadirachtin and/or the cost efficiency of the process. Although the procedure is effective over a broad range of temperatures, the preferred operating temperatures are within the range of 20°–60° C. The treatment is independent of the order of addition of the reactants.

Separation of the precipitate from the solvent/oil mixture is accomplished by a variety of common methods including, but not limited to, vacuum filtration or centrifugation. The precipitate is preferably dried by appropriate means to remove excess solvent. This dried precipitate (azadirachtin concentrate) typically contains between 5% and 30% azadirachtin by weight.

The present invention will become more clear from consideration of the following examples which are set forth to further illustrate the principles of the invention. They are not intended, in any way, to be limitative thereof. Modifications may be made by those skilled in the art without departing from the spirit of the invention. For instance, while the following examples use seeds from the neem tree (*Azadirachta indicia*) as the starting plant material, the invention is operable with other azadirachtin-containing plant materials. All percentages are by weight unless otherwise indicated.

EXAMPLES

Example 1

Effect of Oil-to-Solvent Ratio on the Precipitation of Mechanically Expelled Neem Oil.

Neem oil (0.125% azadirachtin) was obtained from cleaned, shelled neem seeds by mechanical expelling. The oil was then warmed to 50° C. to dissolve all solids. Azadirachtin precipitation was carried out using 40 g aliquots of warmed neem oil, added over a two-minute period to an agitated vessel containing hexanes. The resulting precipitate was stirred in solvent for an additional 20 minutes, collected by filtration, washed with fresh hexanes, and air dried. The analysis of azadirachtin content in the precipitate was determined by HPLC using an external, analytically pure azadirachtin standard as described in, for instance: Uebel, E. C., et al. (1979) "C-18 HPLC" J Liq. Chromatography 2:875; Warthen, J. D. Jr., et al. (1984) J. Liq. Chromatography 7:591; Yamasaki, R. B., et al. (1986) "Phenyl HPLC", J. Chromatography 356:220; and Huang, H. and Morgan, E. D. (1990) "Supercritical Fluid Chromatography" J. Chromatography 519:137. Table 1 shows the effect of varying the ratio of neem oil to hexane on azadirachtin precipitation.

TABLE 1

Effect of Neem Oil to Solvent Ratio on Azadirachtin Precipitation

| Oil/Hexane Ratio (v/v) | % Azadirachtin in Precipitate | % Recovery of Azadirachtin |
|---|---|---|
| 1/1 | 9.66 | 63 |
| 1/4 | 8.13 | 76 |
| 1/6 | 10.07 | 74 |

Example 2

Effect of Addition Time on the Precipitation of Mechanically Expelled Neem Oil.

The same procedures were followed as in Example 1 above except that approximately 183 g of neem oil (0.125% azadirachtin) was added to 800 ml of hexanes, and the time over which the oil was added to the hexanes was varied from 3 to 2020 seconds. Results are shown in Table 2.

TABLE 2

Effect of Addition Time on Azadirachtin Precipitation

| Addition Time (sec.) | % Azadirachtin in Precipitate | % Recovery of Azadirachtin |
|---|---|---|
| 3 | 10.13 | 74 |
| 99 | 12.16 | 77 |
| 356 | 11.35 | 83 |
| 1136 | 9.12 | 92 |
| 2020 | 10.85 | 79 |

Example 3

Effect of Solvent Temperature on the Precipitation of Mechanically Expelled Neem Oil.

The same procedures as in Example 1 were followed except that oil addition time was 4 minutes; the amounts of reagents were 182 g neem oil and 800 ml hexanes; and hexane temperature was varied from 1° C. to 40° C. The calculated weight of azadirachtin in each oil sample was 0.228 g. Results are shown in Table 3.

TABLE 3

Effect of Hexane Temperature on Precipitation of Mechanically Expelled Neem Oil

| Solvent Temperature (°C.) | % Azadirachtin in Precipitate | % Recovery of Azadirachtin |
|---|---|---|
| 1 | 8.90 | 79 |
| 15 | 9.42 | 83 |
| 20 | 9.95 | 74 |
| 40 | 12.36 | 70 |

Example 4

Precipitation of Concentrated Neem Extract by Inverse Addition of Hexane to Neem Oil, and the Effect of Hexane-to-Oil Ratio.

Forty (40) g of mechanically expelled neem oil (0.050 g azadirachtin) was warmed to 50° C., then stirred while hexanes were added over a two-minute period. The mixture was stirred for an additional 20 minutes, then filtered, dried and assayed as above. Results are shown in Table 4.

TABLE 4

Effect of Ratio and Order of Addition of Hexane and Neem Oil on Azadirachtin Precipitation

| Oil/Hexane Ratio (v/v) | % Azadirachtin in Precipitate | % Recovery of Azadirachtin |
|---|---|---|
| 1/1 | 9.75 | 42 |
| 1/4 | 10.04 | 86 |
| 1/6 | 11.22 | 88 |

Example 5

Solvent Extraction of Expelled Neem Cake

A 1.1 kg sample of expelled neem cake was extracted in a Soxhlet extractor with 4 liters of ethylene dichloride at reflux for 18 hours to remove residual neem oil and azadirachtin. The solution was filtered, the solvent was removed under vacuum, and the oil (260 ml) was assayed for azadirachtin content as described in Example 1. The extracted oil contained 0.31% azadirachtin.

Example 6

Effect of Oil-to-Solvent Ratio on the Precipitation of Solvent-Extracted Neem Oil.

Solvent-extracted neem oil (113 g) prepared according to Example 5 was warmed to 50° C., transferred to an addition funnel, and added over a period of about four minutes to a magnetically stirred flask of hexanes at 25° C. The precipitated material was stirred an additional 20 minutes, then filtered, air dried, and analyzed for azadirachtin content as described in Example 1. Table 5 shows the effect of variation in oil-to-hexane ratio on precipitation of solvent-extracted neem oil.

TABLE 5

Effect of Oil-to-Hexane Ratio on Precipitation of Azadirachtin from Solvent-Extracted Neem Oil

| Oil/Hexane Ratio (v/v) | % Azadirachtin in Precipitate | % Recovery of Azadirachtin |
|---|---|---|
| 1/1 | 8.76 | 77 |
| 1/4 | 8.38 | 89 |
| 1/6 | 8.03 | 86 |

Example 7

Effect of Temperature on the Precipitation of Solvent-Extracted Neem Oil.

Solvent-extracted neem oil (113 g) prepared according to Example 5 was warmed to 50° C. and added over a four-minute period to an agitated vessel containing hexanes at the temperatures listed below. The final oil-to-solvent ratio in each case was 1:3. Table 6 illustrates the effect of solvent temperature on azadirachtin yield.

TABLE 6

Effect of Hexane Temperature on Azadirachtin Precipitation of Solvent-Extracted Neem Oil

| Hexane Temperature (°C.) | % Azadirachtin in Precipitate | % Recovery of Azadirachtin |
|---|---|---|
| 0 | 7.35 | 89 |
| 15 | 6.35 | 83 |
| 25 | 7.78 | 83 |
| 40 | 8.21 | 82 |

Example 8

Azadirachtin Precipitation using Mechanically Expelled Neem Oil.

One metric ton of decorticated neem seed kernel was processed using a commercial oil expeller to remove approximately 80% of the neem oil. The expelling step yielded approximately 300 kg of neem oil and approximately 700 kg of neem kernel cake. The oil was slowly added to an agitated vessel containing 1200 liters of hexanes. The polar materials in the oil, including azadirachtin, precipitated out in solid form. The solid precipitate was then collected by filtration and air dried. The dried azadirachtin concentrate (1.8 kg) contained approximately 220 g (12%) azadirachtin.

Example 9

Ethyl Acetate Extraction and Hexane Precipitation of Neem Seed Kernel.

Decorticated neem seed kernel (500 g) was ground in a blender in the presence of ethyl acetate. The mixture of ground neem seed kernel and ethyl acetate was transferred to a flask containing two additional liters of ethyl acetate. The mixture was stirred for five hours at 60° C., then filtered through celite and sand. The filtrate was concentrated and added to one liter of stirred hexanes. The dried azadirachtin concentrate (5.83 g) was collected by filtration and found to contain 0.51 g (8.8%) azadirachtin.

Example 10

The Effect of Solvent Type on Azadirachtin Precipitation.

Two 1.1 kg samples of expelled neem kernel cake were extracted in a Soxhlet extractor with ethylene dichloride (EDC) for 18 hours. The two extracts were combined, the EDC removed under vacuum, and the residual oil assayed for azadirachtin content as described in Example 1. The chemically extracted oil contained 1.39% azadirachtin. Approximately 70 g of extracted oil was warmed to 50° C., then added with stirring over a 2.5-minute period to 225 ml of the respective non-polar solvents listed in Table 7. The mixture was then stirred an additional 15 minutes, filtered, washed with fresh non-polar solvent, dried and assayed as above. Results are summarized in Table 7.

TABLE 7

Effect of Solvent On Precipitation

| Non-Polar Solvent | % Azadirachtin in Precipitate | % Recovery of Azadirachtin |
|---|---|---|
| Hexanes | 17.37 | 97 |
| Heptanes | 17.46 | 83 |
| Octanes | 16.58 | 64 |
| Low Boiling Petroleum Ethers | 17.16 | 83 |
| High Boiling Petroleum Ethers | 14.67 | 87 |
| Paraffin Oil | 15.00 | 83 |
| Aromatic Naptha | 20.62 | 66 |

I claim:

1. A method for preparing an azadirachtin-containing concentrate from an azadirachtin-containing plant oil which method comprises mixing with said oil a sufficient amount of a non-polar solvent in which azadirachtin has low solubility to produce an azadirachtin-containing precipitate, thereby precipitating said azadirachtin-containing concentrate.

2. A method according to claim 1 wherein said non-polar solvent is a hydrocarbon selected from the group consisting of aliphatic, aromatic and alicyclic hydrocarbons, and mixutres thereof.

3. A method according to claim 1 wherein the hydrocarbon is selected from the group consisting of pentanes, hexanes, heptanes, octanes, nonanes and decanes, and mixtures thereof.

4. A method according to claim 1 wherein said non-polar solvent is selected from the group consisting of hexanes, heptanes and petroleum ethers.

5. A method according to claim 1 wherein said azadirachtin-containing plant oil is a neem oil.

6. A method for preparing an azadirachtin-containing concentrate comprising the steps of:

(a) grinding, flaking or pressing an azadirachtin-containing plant material to produce an azadirachtin-containing expelled oil and a solid expeller cake;

(b) optionally repeating step (a) to remove additional plant oils and azadirachtin from said expeller cake;

(c) mixing the expelled oil with a sufficient amount of a non-polar solvent in which azadirachtin has low solubility to produce an azadirachtin-containing preciptate, thereby precipitating said azadirachtin-containing concentrate; and (d) collecting the azadirachtin-containing concentrate.

7. A method according to claim 6 wherein said non-polar solvent is a hydrocarbon selected from the group consisting of aliphatic, aromatic and alicyclic hydrocarbons, and mixtures thereof.

8. A method according to claim 7 wherein the hydrocarbon is selected from the group consisting of pentanes, hexanes, heptanes, octanes, nonanes and decanes, and mixtures thereof.

9. A method according to claim 6 wherein said non-polar solvent is selected from the group consisting of hexanes, heptanes and petroleum ethers.

10. A method according to claim 6 wherein said collecting is accomplished by decantation, filtration, centrifugation, or a combination thereof.

11. A method according to claim 6 wherein the azadirachtin-containing concentrate from step (d) is dried to remove excess solvent.

12. A method according to claim 6 wherein said azadirachtin-containing plant material is a neem seed material.

13. A method for preparing an azadirachtin-containing concentrate comprising the steps of:

(a) mixing an azadirachtin-containing plant material with a polar solvent, thereby forming an extract containing azadirachtin and plant oil;

(b) optionally repeating step (a) to remove additional plant oil and azadirachtin from said plant material;

(c) removing excess polar solvent from said extract to yield an azadirachtin-containing plant oil;

(d) mixing said extracted oil with a sufficient amount of a non-polar solvent in which azadirachtin has low solubility to produce an azadirachtin-containing precipitate, thereby precipitating said azadirachtin-containing concentrate; and (e) collecting the azadirachtin-containing concentrate.

14. A method according to claim 13 wherein said polar solvent is selected from the group consisting of ketones, alcohols, esters, ethers, nitriles, amides, sulfoxides, substituted aliphatic hydrocarbons, aromatic hydrocarbons, and substituted aromatic hydrocarbons, and mixtures thereof.

15. A method according to claim 13 wherein said polar solvent is selected from the group consisting of acetone, benzene, dichloromethane, ethanol, ethyl acetate, ethylene dichloride, methanol, methyl acetate, methyl t-butyl ether, methyl formate, 2-propanol, toluene and xylene, and mixtures thereof.

16. A method according to claim 13 wherein said polar solvent is ethylene dichloride or dichloromethane.

17. A method according to claim 13 wherein said non-polar solvent is a hydrocarbon selected from the group consisting of aliphatic, aromatic and alicyclic hydrocarbons, and mixtures thereof.

18. A method according to claim 17 wherein the hydrocarbon is selected from the group consisting of pentanes, hexanes, heptanes, octanes, nonanes and decanes, and mixtures thereof.

19. A method according to claim 13 wherein said non-polar solvent is selected from the group consisting of hexanes, heptanes and petroleum ethers.

20. A method according to claim 13 wherein the azadirachtin-containing concentrate from step (e) is dried to remove residual solvents.

21. A method according to claim 13 wherein said azadirachtin-containing plant material is a neem seed material.

22. A method for preparing an azadirachtin-containing concentrate comprising the steps of:

(a) grinding, flaking or pressing an azadirachtin-containing plant material to produce a mechanically expelled azadirachtin-containing oil and a solid expeller cake;

(b) mixing the expeller cake with a suitable polar solvent, thereby forming an extract containing azadirachtin and plant oil;

(c) optionally repeating one or both of steps (a) and (b) to remove additional azadirachtin and plant oil;

(d) removing excess solvent from said extract to yield an azadirachtin-containing plant oil;

(e) mixing the expelled oil or extracted oil, either individually or combined, with a sufficient amount of a non-polar solvent in which azadirachtin has low solubility to produce an azadirachtin-containing precipitate, thereby precipitating an azadirachtin-containing concentrate; and (f) collecting the azadirachtin-containing concentrate.

23. A method according to claim 22 wherein said polar solvent is selected from the group consisting of ketones, alcohols, esters, ethers, nitriles, amides, sulfoxides, substituted aliphatic hydrocarbons, aromatic hydrocarbons and substituted aromatic hydrocarbons, and mixtures thereof.

24. A method according to claim 22 wherein said polar solvent is selected from the group consisting of acetone, benzene, dichloromethane, ethanol, ethyl acetate, ethylene dichloride, methanol, methyl acetate, methyl t-butyl ether, methyl formate, 2-propanol, toluene and xylene, and mixtures thereof.

25. A method according to claim 22 wherein said polar solvent is ethylene dichloride or dichloromethane.

26. A method according to claim 22 wherein said non-polar solvent is a hydrocarbon selected from the group consisting of aliphatic, aromatic and alicyclic hydrocarbons, and mixtures thereof.

27. A method according to claim 26 wherein the hydrocarbon is selected from the group consisting of pentanes, hexanes, heptanes, octanes, nonanes and decanes, and mixtures thereof.

28. A method according to claim 22 wherein said non-polar solvent is selected from the group consisting of hexanes, heptanes and petroleum ethers.

29. A method according to claim 22 wherein the azadirachtin-containing concentrate from step (f) is dried to remove excess solvent.

30. A method according to claim 22 wherein said azadirachtin-containing plant material is a neem seed material.

31. A method for preparing a precipitate fraction of neem oil comprising the steps of:

(a) mixing said neem oil with a sufficient amount of a non-polar solvent to form a precipitate;

(b) collecting said precipitate; and optionally (c) drying the precipitate from step (b) to remove residual solvent.

32. A method according to claim 31 wherein said non-polar solvent is a hydrocarbon selected from the group consisting of aliphatic, aromatic and alicyclic hydrocarbons, and mixtures thereof.

33. A method according to claim 32 wherein the hydrocarbon is selected from the group consisting of pentanes, hexanes, heptanes, octanes, nonanes and decanes, and mixtures thereof.

34. A method according to claim 31 wherein said non-polar solvent is selected from the group consisting of hexanes, heptanes and petroleum ethers.

* * * * *